Sept. 5, 1944. L. REICHERT Plant Pat. 640
CHRYSANTHEMUM PLANT
Filed Feb. 10, 1944
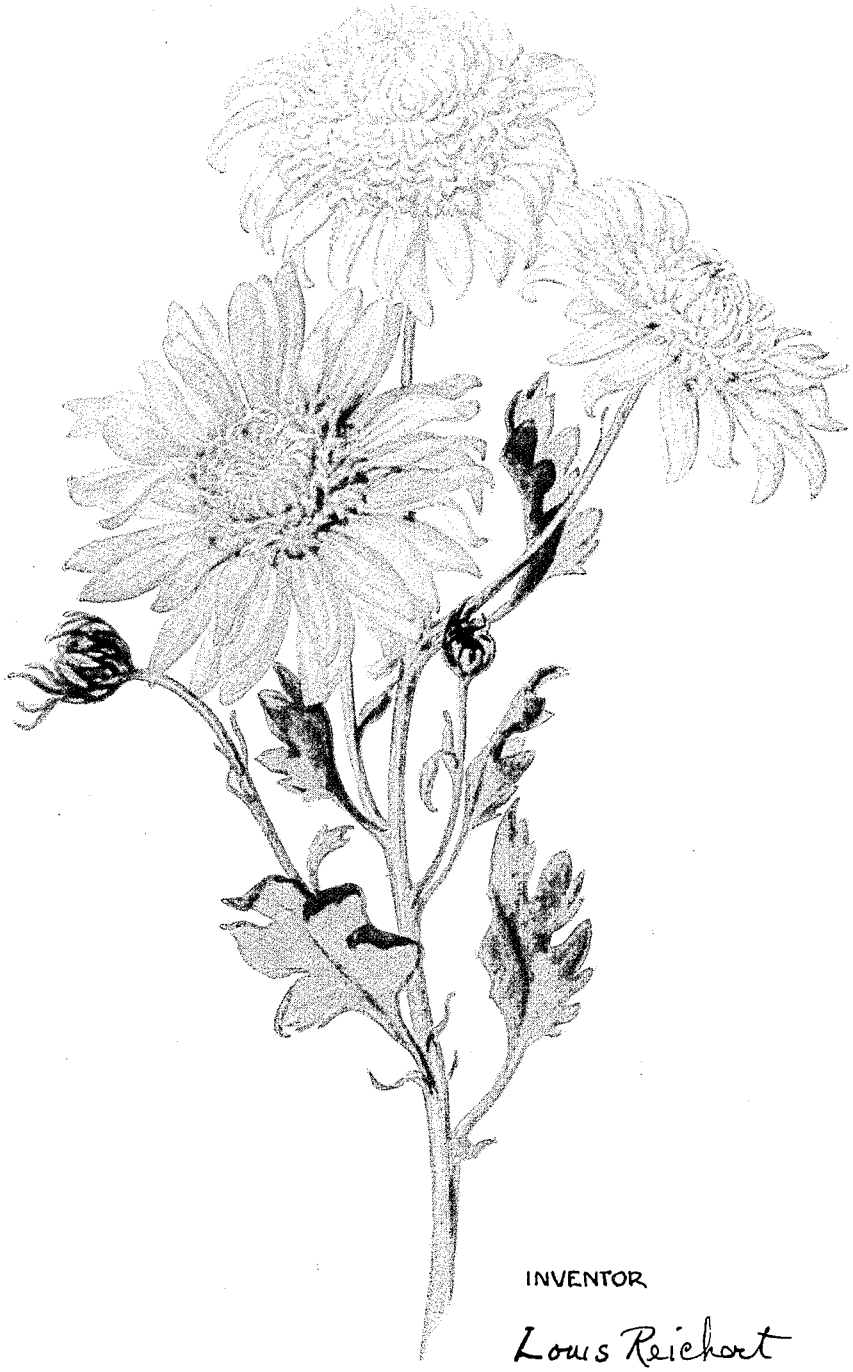
INVENTOR
Louis Reichert
By Orville M Kile
PLANT PATENT AGENT Patented Sept. 5, 1944

Plant Pat. 640

UNITED STATES PATENT OFFICE

640

CHRYSANTHEMUM PLANT

Louis Reichert, Belle Harbor, N. Y.

Application February 10, 1944, Serial No. 521,854

1 Claim. (Cl. 47—60)

My present invention is an improved variety of anemone type Korean chrysanthemum which was discovered by me in my garden. It originated as a seedling resulting from hybridizing by bees among various types of Korean chysanthemums and its parentage is unknown except that both parents were Korean varieties. The new variety has been reproduced by means of cuttings and its characteristics have proved to be permanent.

My new variety differs radically from all other known anemone type Korean chrysanthemums, principally because it is hardy and early. These two features extend both ends of the blooming season, as well as permit the plant to "winter over" in cold climates without danger.

Also notable is the extremely large center of the flowers which has the effect of rich tapestry. Added to these desirable new features, the very pleasing color herein indicated, and there is presented the first good, really outstanding anemone-type Korean chrysanthemum that has yet appeared.

With the exception of the above-mentioned features, my new variety appears to be like other anemone-type Korean chrysanthemums.

The accompanying illustration which is a part of this application and specification, portrays three specimens of my new variety in various stages of development, slightly enlarged in the original.

Following is a brief detailed description of this new variety. Color plate references indicate Ridgway's Color Standards and Nomenclature.

*The plant*

Growth: Vigorous and healthy, attaining a height of 12 to 15 inches when grown in the open.

Cold resistance: Extremely hardy-hardier than any other known Korean chrysanthemum variety.

Disease resistance: Very resistant to diseases.

Propagation: Variety propagates very easily.

Blooming habits: Very prolific. Flowers are produced in clusters of from 3 to 8 flowers.

Blooming period: Blooming dates of course vary with the season and the climate but my new variety blooms earlier than any other known anemone type Korean chrysanthemum, and extends the blooming season longer because of the hardiness of the variety. In this climate the first blooms open in late August or early September and blooms continue to appear up to the end of November and sometimes even to the middle of December.

Stems: Wiry and strong although slender. Approximately Grass Green (Plate VI).

Foliage:

*Size.*—Small (1½ inches long by 1 inch wide is the average).

*Shape.*—Palmately deep-lobed.

*Color.*—Slightly darker than stems.

*The flower*

Bud: Small, round; opens slowly.

Flower: Anemone type.

*Size.*—Attains a size of about 3½ inches in diameter.

*Form.*—Consists of very large cushion surrounded by two or three rows of petals of unequal lengths.

*Cushion.*—Consists of approximately 200 to 250 tubular florets which are set upon a high pithy knob and which develop into two phases. They begin opening at the outer rim of the cushion and proceed slowly toward the center. At the height of the flower's coloring, two or three rows or about 75 of the florets are open showing some of the inner surface of the florets which is approximately Eugenia Red (Plate XIII) edged with a line of yellow. The other florets are unopened and show little more than the yellow outer surface of the florets which at that stage is approximately Wax Yellow (Plate XVI). The entire effect of the cushion is that of a rich tapestry.

*Petals or ray flowers.*—Petals number about 40 to 45 per blossom and extend horizontally from the base of the cushion. They average 1½ inches long and about ¼ inch wide, but only about 1 inch of the length extends beyond the cushion. Their color is approximately Pompeian Red (Plate XIII) when first open, with a slight tip of yellow on some of the petals. As the opened flower grows older, the color ranges through Eugenia Red (Plate XXVIII), Corinthian Red (Plate XXVI), Orange Vinaceous (Plate XXVII), Congo Pink (Plate XXVII), and some even lighten to Buff Pink (Plate XXVIII).

*Bracts.*—The involucre is completed by many overlapping bracts.

*Longevity.*—The flowers last a long time, some of them two or three weeks.

Having thus disclosed my discovery, I claim:

The new and useful variety of anemone type Korean chrysanthemum plant, substantially as herein shown and described, characterized particularly by its winter hardiness; its early and long blooming season; and its flowers having large centers presenting a tapestry-like effect and distinctive color as indicated.

LOUIS REICHERT.